United States Patent
Morita et al.

(10) Patent No.: US 6,265,555 B1
(45) Date of Patent: Jul. 24, 2001

(54) METHOD OF MANUFACTURING COMPOSITIONS WITH HIGH GANGLIOSIDE CONTENT

(75) Inventors: Minoru Morita, Tokyo-to; Makihiro Sugawara, Tokorozawa; Masayuki Eto, Kawagoe; Susumu Miura, Tachikawa; Masanori Kotani, Sayama, all of (JP)

(73) Assignee: Snow Brand Milk Products Co., Ltd., Sapporo (JP)

( * ) Notice: Subject to any disclaimer, the term of this patent is extended or adjusted under 35 U.S.C. 154(b) by 0 days.

(21) Appl. No.: 09/501,541

(22) Filed: Feb. 9, 2000

(30) Foreign Application Priority Data

Feb. 16, 1999 (JP) .................................................. 11-036844

(51) Int. Cl.$^7$ ........................ A61K 31/7032; C07H 15/06
(52) U.S. Cl. ........................ 536/17.9; 536/18.5; 536/124; 536/127; 514/25; 514/54
(58) Field of Search ................................. 536/17.9, 18.5, 536/124, 127; 514/25, 54

(56) References Cited

U.S. PATENT DOCUMENTS 5,795,980 * 8/1998 Hanagata et al. ................... 536/124
5,844,104 * 12/1998 Yanahira et al. ................... 536/18.5

FOREIGN PATENT DOCUMENTS

| 60-072819 | 4/1985 | (JP) . |
| 2-207090 | 8/1990 | (JP) . |
| 9-291094 | 11/1997 | (JP) . |
| 10-218892 | 8/1998 | (JP) . |

* cited by examiner

Primary Examiner—Ralph Gitomer
Assistant Examiner—Leigh C. Maier
(74) Attorney, Agent, or Firm—Knobbe, Martens, Olson & Bear, LLP.

(57) ABSTRACT

A composition with a high ganglioside content is manufactured by a method characterized in that milk or milk-derived material containing ganglioside is dispersed in an ethanol solution so that the concentration of ethanol becomes 60~95%; after removing the precipitate which is generated by heating the solution to a temperature higher than 50° C., the obtained supernatant is cooled to a temperature lower than 0° C; and the obtained precipitate is recovered. The obtained composition with a high ganglioside content is used advantageously as a material for foods and drinks, medicines, chemical products, etc.

8 Claims, No Drawings

METHOD OF MANUFACTURING COMPOSITIONS WITH HIGH GANGLIOSIDE CONTENT

BACKGROUND OF THE INVENTION

1. Field of the Invention

This invention relates to a method of manufacturing a composition with a high ganglioside content easily and quickly. Because the composition with a high ganglioside content that is manufactured by the method of this invention contains ganglioside at a high percentage, it is useful as a material used for various foods and drinks, medicines, chemical products, etc.

2. Description of the Related Art

Ganglioside is a general tenn for sphingoglycolipid that contains sialic acid and it is known that various molecular species exist. In recent years, biochemical research on ganglioside has been conducted actively and its physiological functions such as cell differentiation, nerve function, malignant alteration, viral infection and cell information transmission have been made known. Further, ganglioside is known to be contained in relatively large quantities in animal cell membranes and brains, fat globule membranes and so on.

Conventionally, for methods of manufacturing a composition with a high ganglioside content, a method to obtain fat globule membranes from buttermilk (Japanese Patent Laid-open No. 60-72819) and a method using ion-exchange resin (Japanese Patent Laid-open No. 2-207090) are known. However, the former method has a problem in that it is very difficult to manufacture a composition with a high ganglioside content on an industrial scale and the latter method has a problem in that it is not suitable for volume processing because it uses ion-exchange resin. The inventors of the present invention previously proposed a method using ethanol as an easy method of manufacturing a composition with a high ganglioside content (Japanese Patent Laid-open No. 9-291094).This method is capable of volume manufacture of a composition with a high ganglioside content, but it requires many procedures including a process in which the use of a membrane device is required.

A method to extract ganglioside from animal tissue using ethanol and propanol (Japanese Patent Laid-open No. 10-218892) is also known, but this is a technique that can only be applied to non-dry animal tissue. Using this method, it is difficult to manufacture in volume a composition with a high ganglioside content and it has a drawback that the recovery rate of ganglioside is very low.

Further, a method of preparing a composition with a high ganglioside content using methanol at the laboratory level (Tohru Nakao and Yoshio Hirabayashi, *Ganglioside Research Method I*, p.32, Gakkai-Shuppan Center, 1995) is also known. However, using methanol is hazardous and this method is not suitable for volume manufacture. Moreover, it is difficult to use the composition with a high ganglioside content obtained in this way as a food material.

Consequently, because of the existing circumstances, a method of easily and quickly manufacturing in volume a composition with a high ganglioside content and which can be used as a food material as well, is called for.

SUMMARY OF THE INVENTION

The inventors of the present invention earnestly proceeded with their research to develop a method of easily and quickly manufacturing in volume a composition with a high ganglioside content and which can be used as a food material as well. They discovered that the solubility of ganglioside in ethanol changed largely according to temperature. They also discovered that a composition with a high ganglioside content could be obtained easily and quickly in volume by dispersing a material containing ganglioside in an ethanol solution, raising the liquid's temperature to generate a precipitate, removing the precipitate, cooling a supernatant obtained to generate a precipitate, and recovering the precipitate. These discoveries led to developing this invention.

Consequently, a problem that this invention intends to solve is to provide a method of easily and quickly manufacturing in volume a composition with a high ganglioside content and which is useful as a material for various foods and drinks, medicines, chemical products.

A material containing ganglioside is dispersed in an ethanol solution so that the concentration of ethanol becomes 60~95%, and the solution is stirred at a temperature of 50~90° C. to dissolve the material. With this operation, ganglioside dissolves into ethanol solution and protein settles out. At this time, if the ethanol concentration of the ethanol solution is below 60% or exceeds 95%, the solubility of ganglioside drops and precipitates, and the ganglioside recovery rate drops.

The obtained supernatant containing ganglioside is cooled to a temperature lower than 0° C., preferably lower than −20° C. With this operation, ganglioside precipitates. At this time, if the temperature is higher than 0° C., the solubility of ganglioside does not drop sufficiently, and the ganglioside recovery rate drops.

By recovering the precipitate containing ganglioside obtained in the above- mentioned way, a composition with a high ganglioside content is manufactured.

Further, as materials containing ganglioside, which are used for this invention, internal organs and brains of animals, or dairy products including milk, butterserum, buttermilk, whey and whey protein concentrate (WPC) can be used. These materials containing ganglioside can be used as they are, or can be used by drying or condensing them.

DETAILED DESCRIPTION OF THE PREFERRED EMBODIMENT

In the present invention, a material containing ganglioside is first dispersed in an ethanol solution so that the concentration of ethanol becomes 60~95%, the material is dissolved by stirring at a temperature of 50~90° C., and the precipitate generated is removed. This precipitate containing protein can be removed using a method such as filtration, centrifugal separation, filter press, or decantation. The supernatant obtained is cooled to a temperature lower than 0° C. and the precipitate generated is recovered. This precipitate which contains ganglioside can be recovered using a method such as filtration, centrifugal separation, filter press, or decantation.

In this way, a composition with a high ganglioside content can be easily and quickly manufactured in volume from a material containing ganglioside. The obtained composition with a high ganglioside content can be used as a material for various foods and drinks, medicines, chemical products, etc. by reducing the composition to powder if necessary.

The present invention is explained in more detail by showing examples.

Further, the ganglioside content is determined using a method of Kawakami and others (Biosci. Biotech. Biochem. vol. 58, pp.1314–1315, 1994).

EXAMPLE 1

100g of butterserum was dispersed in 1,000 g of an ethanol aqueous solution with an ethanol concentration of 80%. After heating the solution to 60° C. and stirring it for one hour, a precipitate was removed by a filter press using a flannel cloth at one side. The obtained supernatant was cooled to −20° C., and left undisturbed overnight. By recovering precipitate by filtration using a 5 μm filter, 6.3 g of composition with a high ganglioside content was obtained.

In the obtained composition with a high ganglioside content, ganglioside of 4.7 weight percent per solid content was achieved. Further, because the ganglioside content in the original butterserum was 0.28 weight percent, it was found that in the manufactured composition, the ganglioside content was concentrated 16.8 times.

EXAMPLE 2

By ultrafiltering butterserum to remove lactose, delactose-butterserum was prepared. 100 g of delactose-butterserum was dispersed in 1,000 g of an ethanol aqueous solution with an ethanol concentration of 80%, and after heating the solution to 65° C. and stirring it for 30 minutes, a precipitate was removed by centrifugal separation. The obtained supernatant was then cooled to −20° C. and left undisturbed overnight. By recovering the precipitate by filtration using a flannel cloth at one side, 6.0 g of composition with a high ganglioside content was manufactured.

In the obtained composition with a high ganglioside content, ganglioside of 6.5 weight percent per solid content was achieved. Further, because the ganglioside content in the original delactose-butterserum was 0.65 weight percent, it was found that in the manufactured composition, the ganglioside content was concentrated 10.2 times.

EXAMPLE 3

100 lit. of ethanol with 99.5 % purity was added to 60 lit. of buttermilk, and the mixture was heated up to 60° C. while being stirred well. After stirring the mixture for one more hour, a precipitate was removed by a filter press using a flannel cloth at one side. The obtained supernatant was then cooled to −20° C. and left undisturbed overnight. By recovering the precipitate by filtration using a 5 μm filter, 101 g of composition with a high ganglioside content was obtained.

In the obtained composition with a high ganglioside content, ganglioside of 5.4 weight percent per solid content was achieved. Further, because the ganglioside content in the original buttermilk was 0.1 weight percent, it was found that in the manufactured composition, the ganglioside content was concentrated 54 times. Comparison Example 1 According to a method mentioned in Japanese Patent Laid-open No. 9-291094, a composition with a high ganglioside content was manufactured. 100 lit. of ethanol with 99.5 % purity was added to 60 lit. of buttermilk. After stirring the mixture well, a precipitate containing ganglioside was recovered by centrifugal separation (2,500 rpm). After this precipitate was dissolved in 4 lit. of water, 35 lit. of ethanol was added and a precipitated protein was recovered by centrifugal separation (3,000 rpm) at room temperature. Water was then added to the solution from which protein had been removed, until its total volume became 300 lit. After performing ultrafiltration using an ultrafiltration (UF) membrane (Cefilt /made by Nihon Gaishi) of 500,000 fractionation molecular weight, the concentrated liquid obtained was frozen and dried and 85 g of a composition with a high ganglioside content was obtained. In addition, ultrafiltration was performed under the conditions of: CF of 100 times, DF of three times and an operating temperature of 30° C.

In the obtained composition with a high ganglioside content, ganglioside of 5.9 weight percent per solid content was achieved. Further, because the ganglioside content in the original buttermilk was 0.1 weight percent, it was found that in the manufactured composition, the ganglioside content was concentrated 59 times.

Here, if we compare the method of Example 3 and the method of Comparison Example 1, the concentration rate and the recovery rate are nearly the same, but the method of Example 3 has advantages in that a device necessary for manufacture is very simple and that the time required for the manufacture is very short. In other words, for the method of Example 3, a tank that can be heated and cooled and a filter press are the only equipment necessary. However, for the method of Comparison Example 1, in addition to a tank and a centrifugal separator, an expensive UF membrane device is necessary. Further, as for the time required for the manufacture, while the method of Example 3 took approximately 24 hours, the method of Comparison Example 1 took approximately 48 hours.

According to the method of this invention, a composition with a high ganglioside content can be easily and quickly manufactured in volume and the obtained composition with a high ganglioside content can be provided advantageously as a material for foods and drinks, medicines, chemical products, etc.

What is claimed is:

1. A method of manufacturing a composition containing ganglioside, comprising the steps of:
    dispersing a material containing ganglioside in an ethanol solution to make the concentration of ethanol 60–95%;
    heating said dispersion to a temperature higher than 50° C. to dissolve ganglioside and simultaneously generate a first precipitate containing proteins;
    removing the first precipitate;
    cooling a supernatant excluding said first precipitate to a temperature lower than 0° C. to generate a second precipitate containing ganglioside; and
    recovering the second precipitate.

2. The method as claimed in claim 1, wherein said material containing ganglioside is milk or a milk-derived material.

3. The method according to claim 1, wherein, in the heating step, the solution is heated to a temperature of 50–90° C.

4. The method according to claim 1, wherein, in the removing step, the first precipitate is removed by filtration, centrifugal separation, filter press, or decantation.

5. The method according to claim 1, wherein, in the removing step, the second precipitate is removed by filtration, centrifugal separation, filter press, or decantation.

6. The method according to claim 1, wherein the material containing ganglioside is selected from the group consisting of milk, butterserum, buttermilk, whey, and whey protein concentrate.

7. The method according to claim 1, wherein, in the heating step, the solution is heated to a temperature of 60° C. or higher.

8. The method according to claim 1, wherein, in the cooling step, the supernatant is cooled to a temperature of −20° C. or lower.

* * * * *